(12) United States Patent
Wu

(10) Patent No.: US 10,986,199 B2
(45) Date of Patent: Apr. 20, 2021

(54) METHOD FOR TRACKING PERSONS AND STATE OF TRACKED PERSON AND DEVICE EMPLOYING METHOD

(71) Applicant: Chiun Mai Communication Systems, Inc., New Taipei (TW)

(72) Inventor: Kuang-Hui Wu, New Taipei (TW)

(73) Assignee: Chiun Mai Communication Systems, Inc., New Taipei (TW)

( * ) Notice: Subject to any disclaimer, the term of this patent is extended or adjusted under 35 U.S.C. 154(b) by 0 days.

(21) Appl. No.: 16/838,216

(22) Filed: Apr. 2, 2020

(65) Prior Publication Data
US 2020/0322439 A1 Oct. 8, 2020

(30) Foreign Application Priority Data
Apr. 2, 2019 (CN) .......................... 201910262873.2

(51) Int. Cl.
| | |
|---|---|
| G08B 23/00 | (2006.01) |
| H04L 29/08 | (2006.01) |
| A61B 5/11 | (2006.01) |
| A61B 5/00 | (2006.01) |
| G06F 1/16 | (2006.01) |
| H04W 4/029 | (2018.01) |
| G01S 13/02 | (2006.01) |
| H04W 4/80 | (2018.01) |
| G16H 40/67 | (2018.01) |
| A61B 5/01 | (2006.01) |

(52) U.S. Cl.
CPC ............ *H04L 67/22* (2013.01); *A61B 5/0022* (2013.01); *A61B 5/01* (2013.01); *A61B 5/1118* (2013.01); *G01S 13/02* (2013.01); *G06F 1/163* (2013.01); *G16H 40/67* (2018.01); *H04W 4/029* (2018.02); *H04W 4/80* (2018.02)

(58) Field of Classification Search
CPC .......................... G08G 1/096716; H04L 67/22
USPC .......... 340/573.1, 573.4, 517, 521, 540, 541
See application file for complete search history.

(56) References Cited

U.S. PATENT DOCUMENTS

| | | | |
|---|---|---|---|
| 6,796,799 B1 * | 9/2004 | Yoshiike | G16H 50/20 434/236 |
| 2007/0030115 A1 | 2/2007 | Itsuji et al. | |
| 2018/0103352 A1 * | 4/2018 | Murase | G01S 5/021 |

FOREIGN PATENT DOCUMENTS

| | | |
|---|---|---|
| CN | 103425971 | 12/2013 |
| CN | 107230317 | 10/2017 |
| CN | 109091118 | 12/2018 |
| TW | M475581 | 4/2014 |

* cited by examiner

*Primary Examiner* — Tai T Nguyen
(74) *Attorney, Agent, or Firm* — ScienBiziP, P.C.

(57) ABSTRACT

A method for remotely monitoring persons and their behavior applies to a person wearing an electronic device which is tracked. The method includes sensing posture and changes in posture of the person within a tracking area to generate posture sensing signals, acquiring wireless signals of the electronic device and further obtaining changes in position of the person according to signal strength of the wireless signals of the electronic device, and transmitting the posture sensing signals and the changes in position of the person to at least one server to analyze and identify the position and behavior of the person and issue warning to caregiver if appropriate. A behavior tracking device is also provided.

18 Claims, 4 Drawing Sheets

METHOD FOR TRACKING PERSONS AND STATE OF TRACKED PERSON AND DEVICE EMPLOYING METHOD

FIELD

The subject matter herein generally relates to behavior tracking.

BACKGROUND

Elderly people, medical patients, or children may fall in places such as rooms, toilets, corridors, etc. If they lose consciousness or cannot call for help, serious injuries may occur because rescue is delayed. Currently, cameras combined with back-end image analysis are used to identify human behavior to avoid the above described incidents. However, when using cameras for detection, it may be difficult to overcome obstructions on the line of sight of the camera, and such a use a camera may also violate personal privacy.

Thus, there is a need for improvement.

BRIEF DESCRIPTION OF THE DRAWINGS

Implementations of the present disclosure will now be described, by way of embodiments, with reference to the attached figures.

DETAILED DESCRIPTION

Figure 1:
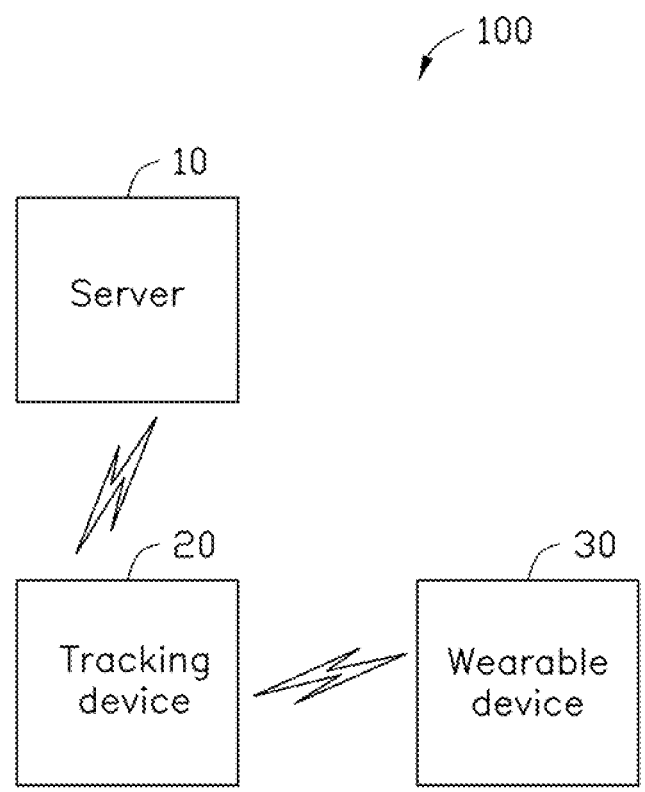
FIG. 1 is a block diagram of an embodiment of a system for tracking persons and their behavior.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure. It should be noted that references to "an" or "one" embodiment in this disclosure are not necessarily to the same embodiment, and such references mean "at least one".

Several definitions that apply throughout this disclosure will now be presented.

The connection can be such that the objects are permanently connected or releasably connected. The term "comprising," when utilized, means "including, but not necessarily limited to"; it specifically indicates open-ended inclusion or membership in the so-described combination, group, series, and the like.

FIG. 1 illustrates a system for tracking persons and their state and behavior (behavior tracking system 100) in accordance with an embodiment. The behavior tracking system 100 may comprise at least one server 10, at least one tracking device 20 (behavior tracking device), and at least one wearable device 30.

In one embodiment, the tracking device 20 can be installed in a predetermined area, and the predetermined area may be an area in building or an outdoor area, such as a hospital area, an outdoor area near a hospital, a nursing home, an area near a nursing home, or an area inside or outside a hotel. The tracking device 20 is configured to track people as objects, for example, elderly people, patients, and children. If a behavior of an object person is determined to be abnormal, an alarm signal can be outputted. One of the at least one wearable device 30 can be carried or worn by each object person.

Figure 2:
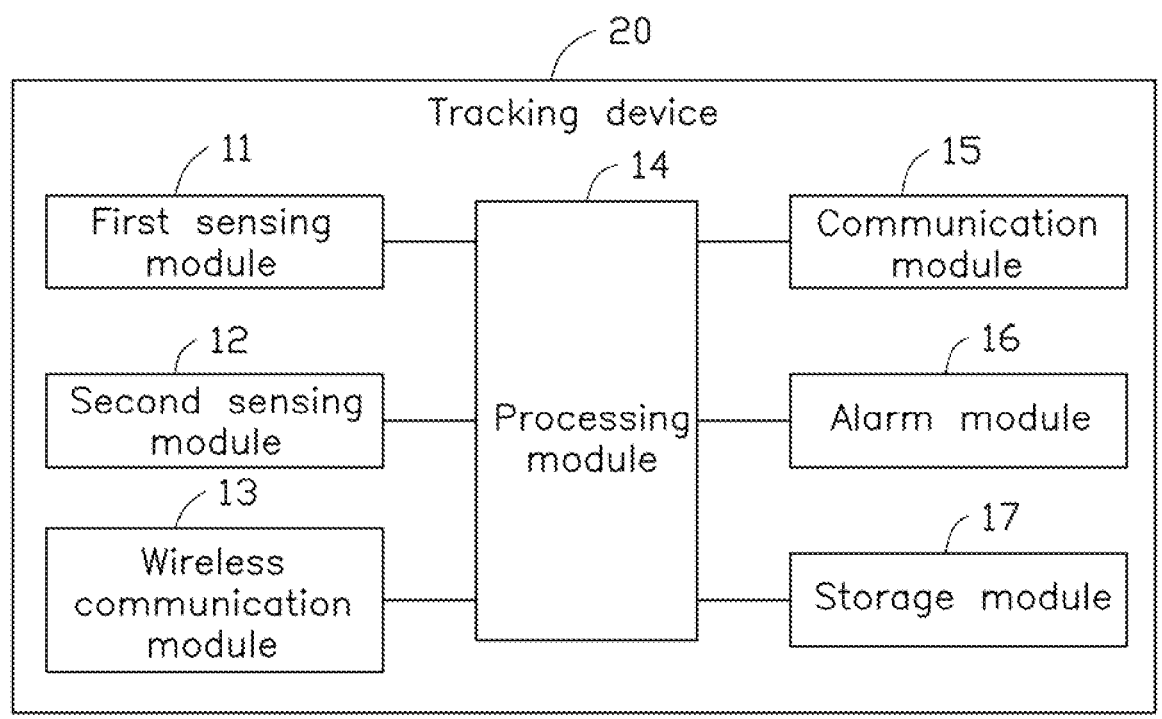
FIG. 2 is a block diagram of an embodiment of a tracking device of the system of FIG. 1.

Referring to FIG. 2, the tracking device 20 may comprise a first sensing module 11, a second sensing module 12, a wireless communication module 13, a processing module 14, a communication module 15, an alarm module 16, and a storage module 17. The first sensing module 11 and the second sensing module 12 may be installed in the tracking device 20 or connected to the tracking device 20 by a wireless/wired connection.

In one embodiment, the first sensing module 11 and the second sensing module 12 may be installed on a wall or a ceiling of a building of the predetermined area.

In one embodiment, the first sensing module 11, the second sensing module 12, the wireless communication module 13, the processing module 14, the communication module 15, the alarm module 16, and the storage module 17 may be integrated into an indoor wireless base station.

In one embodiment, the first sensing module 11 comprises a millimeter wave sensor. The first sensing module 11 is configured to sense changes in position and changes in posture of an object within a tracking area and generate changes in position signals and posture signals.

When a current position of the object within the tracking area is tracked by the millimeter wave sensor, the processing module 14 can calculate changes in position of the object within the tracking area. When a millimeter wave signal is reflected from the object within the tracking area, the processing module 14 can calculate posture changes of the object within the tracking area. For example, the posture changes may comprise a walking state posture, a posture when lying down, a stationary or standing state, and changes in such states.

The wireless communication module 13 is configured to acquire basic information of the wearable device 30. Then, the changes in position of the object can be calculated by the wireless communication module 13 according to the basic information of the wearable device 30. The basic information of the wearable device 30 may comprise strength of wireless signals, an identification code, and battery information. The wireless communication module 13 may be a BLUETOOTH unit, a WI-FI unit, or a ZIGBEE unit. For example, an indoor or outdoor positioning function can be realized through analyzing online signals among at least three wireless communication modules 13 and the wearable device 30.

In one embodiment, the wearable device 30 is worn or carried by the object. The wireless communication module 13 may obtain the changes in position of the object by determining whether wireless signals sent by the wearable device 30 are received. For example, if the wireless communication module 13 does not receive the wireless signals sent from the wearable device 30, it indicates that the object may have left the tracking area. So long as the wireless communication module 13 receives the wireless signals sent from the wearable device 30, it indicates that the object is within the tracking area.

In one embodiment, the wearable device 30 sends the wireless signals automatically at a fixed frequency or the person (carrying the wearable device 30) manually sends the wireless signals.

In one embodiment, the wearable device 30 may comprise a G-sensor (gravity sensor) and a GPS (Global Positioning System) module. The wearable device 30 can detect a moving of the object through the G-sensor or the GPS module. The wearable device 30 can change a frequency of the wireless signals to indicate a state and a change thereof.

In one embodiment, if a user wears the wearable device 30 and moves indoors, and the GPS signal may not be received. The G-sensor can count the number of steps of the user, and the frequency of the wireless signals can be adjusted based on the counting by the G-sensor. For example, if the G-sensor detects that the user is continuously moving, the wireless signals can be sent at a shorter period as a frequency. If the G-sensor detects that the user stops moving, the wireless signals can be sent at a longer frequency.

In one embodiment, if the user carries the wearable device 30 and moves outdoors, the GPS signal may be resumed. A moving direction and a moving distance of the user can be detected by the GPS module, and the frequency of the wireless signals can be adjusted based on detection by the GPS module. For example, if the GPS module detects that the user is continuously moving, the wireless signals are sent at a shorter frequency. If the user stops moving as detected by the G-sensor or the GPS position signal remains unchanged in a period of time, the wireless signals are sent at a longer frequency.

The processing module 14 is configured to control the communication module 15 to transmit posture sensing signals and the changes in position of the object to the server 10 to identify the state and behavior of the object.

In one embodiment, the communication module 15 can transmit the posture sensing signals sensed by the first sensing module 11 and the changes in position obtained by the wireless communication module 13 to the server 10. The server 10 can analyze the posture sensing signals and the changes in position of the object to obtain the state and behavior of the object.

In one embodiment, the communication module 15 can be a wired communication unit or a wireless communication unit. The processing module 14 can be a data processing chip, such as a microprocessor or a central processing unit (CPU). The storage module 17 may store control instructions, and the processing module 14 may load and run the control instructions stored by the storage module 17 to implement a control function, such as a function of behavior tracking.

The server 10 receives the posture sensing signals and the changes in position of the object and analyzes the received data by using an analytic algorithm or the like, to identify the behavior of the object. The analytic algorithm may be configured to analyze changes in posture and/or position. For example, the server 10 may determine whether the object is in a walking state, a lying down state, or a stationary or standing state based on the posture sensing signals. The server 10 may determine whether the object leaves the tracking area based on the posture sensing signals and the changes in position.

The server 10 can determine whether the behavior of the object is abnormal. For example, the object is an elderly person or a patient, if the behavior of the elderly person or the patient changes from a walking state to a lying down state, the server 10 may determine that the object has collapsed or fallen.

In one embodiment, multiple first sensing modules 11 and multiple second sensing modules 12 are installed on walls or ceilings of multiple rooms of a specified building, such as an inpatient building of a hospital. The first sensing modules 11 and the second sensing modules 12 in different rooms or corridors have different position identification. If an object is determined to be fallen down, a fall area of the object can be determined according to the position identification of the first sensing module 11. For example, the fall area can be a ward, a toilet, a bathroom, etc. The server 10 can output an alarm control signal to the tracking device 20 when the object is determined to be in an abnormal behavior, and the processing module 14 can control the alarm module 16 to output alarm information according to the alarm control signal.

In one embodiment, the alarm information outputted by the alarm module 16 may warn specific persons to focus on the current state of the object. The specific persons may be family members, nurses, caregivers, etc.

In one embodiment, the server 10 can analyze the posture sensing signals to obtain the changes in posture of the object. Then, bedtime schedule, pressure ulcer prevention, or other nursing functions can be achieved. For example, if the object is a patient with a special condition and needs to be turned over regularly, the server 10 may communicate with the tracking device 20 based on the posture sensing signals in combination with time information to output a reminder to turn over.

In one embodiment, the first sensing module 11 comprises the millimeter wave sensor, the first sensing module 11 may be further configured to sense physiological information of the object, such as a heartbeat, a breathing, a quality of sleep, etc. The processing module 14 is further configured to control the communication module 15 to transmit the physiological information to the server 10. The server 10 can determine whether physiological features of the object are abnormal according to the physiological information. The server 10 can output a corresponding alarm control signal to the tracking device 20 if one or more physiological features of the object are determined to be abnormal. The processing module 14 can control the alarm module 16 to output a reminder of abnormal physiological feature according to the alarm control signal to warn the specific persons.

The second sensing module 12 may comprise an infrared sensor for sensing body temperature information of the object. The processing module 14 is further configured to control the communication module 15 to transmit the body temperature information to the server 10. The server 10 can determine whether the body temperature of the object is abnormal based on the body temperature information. If the body temperature of the object is abnormal, the server 10 can output a corresponding alarm control signal to the tracking device 20, the alarm module 16 can output a reminder of abnormal body temperature to warn the specific persons.

In one embodiment, the infrared sensor can be an array infrared sensor module. For example, the array infrared sensor module is an array size of N*N (N is greater than or equal to 1). The temperature of the object can be sensed by multi-point infrared sensor, such as sensing the body temperature of the object.

As mentioned, when the multiple first sensing modules 11 and the multiple second sensing modules 12 are installed on multiple walls or ceilings of the building, blind spots during tracking can be avoided, and the privacy of the object will not be violated. If the object is a patient, the body temperature of the patient can be measured in real time through the second sensing module 12, and the heartbeat, the breathing, or other physiology of the object can be monitored in real time through the first sensing module 11. When an abnormal state of the patient is sensed, corresponding alarm information (for example, a fallen alarm, body temperature alarm, heart rate too fast/too slow alarm, etc.) is outputted, which can reduce the workload of nursing staff.

In one embodiment, if the second sensing module 12 is installed on the wall or the ceiling, a sensing distance can exist between the object and the second sensing module 12. An error in sensing may occur in the body temperature information of the object measured by the second sensing module 12, and the server 10 is further configured to perform a temperature compensation on the body temperature information sensed by the second sensing module 12 according to a predetermined temperature compensation algorithm and the sensing distance between the object and the tracking device 20 to obtain an actual body temperature of the object.

For example, a distance between the object and the tracking device 20 can be sensed by the first sensing module 11. The communication module 15 is further configured to transmit the distance between the object and the tracking device 20 to the server 10, and the server 10 can perform the temperature compensation on the body temperature information sensed by the second sensing module 12 based on the known distance to obtain the actual body temperature of the object.

Figure 3:
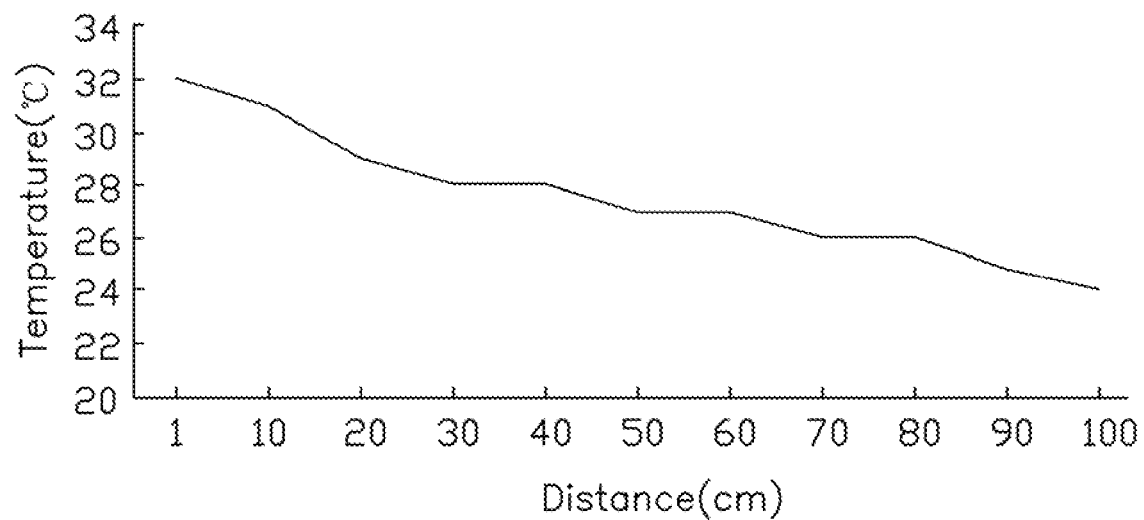
FIG. 3 is a temperature-distance curve of an embodiment of temperature information of an object as sensing distance changes sensed by a second sensing module of the device of FIG. 2.

Referring to FIG. 3, at the same temperature, different distances between the second sensing module 12 and the object can cause different sensing. For example, if the distance between the second sensing module 12 and the object is 1 cm, the temperature information is sensed to be 32 degrees, if the distance between the second sensing module 12 and the object is 30 cm, the temperature information is sensed to be 28 degrees, if the distance between the second sensing module 12 and the object is 70 cm, the temperature information is sensed to be 26 degrees, and if the distance between the second sensing module 12 and the object is 100 cm, the temperature information is sensed to be 24 degrees.

For other temperature values, such as 33 degrees or 36 degrees, a temperature-distance curve similar to that in FIG. 3 can also be employed. The server 10 may use a plurality of pre-stored temperature-distance curves to perform the temperature compensation on the body temperature information sensed by the second sensing module 12 to obtain the actual body temperature of the object.

Figure 4:
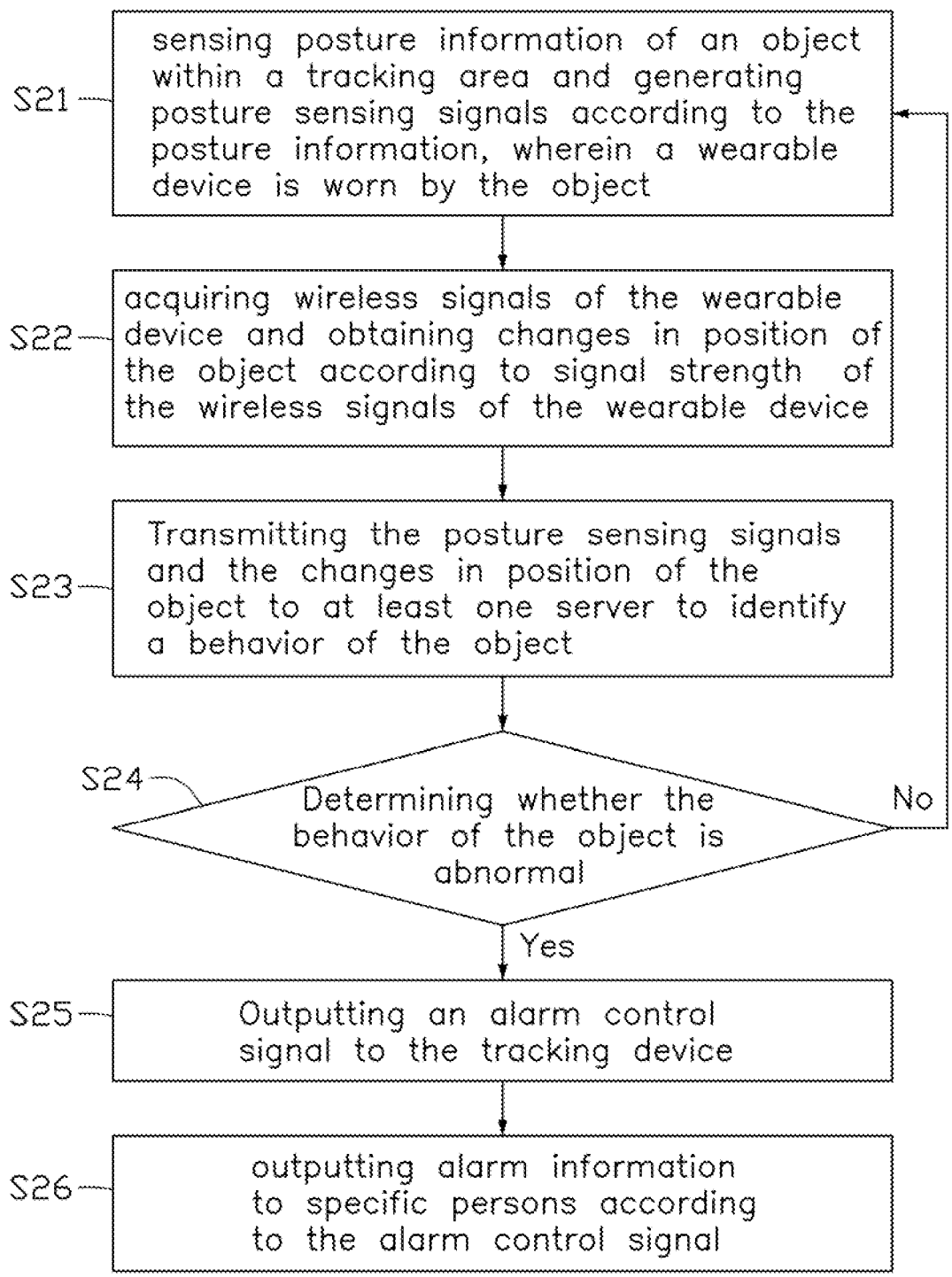
FIG. 4 is a flow diagram of an embodiment of a method for tracking persons and their behavior which is utilized in the device of FIG. 2.

FIG. 4 illustrates one embodiment of a behavior tracking method. The method can be configured to track the object, for example, to determine whether a behavior of the object is abnormal, and output an alarm information if the behavior of the object is determined to be abnormal. The flowchart presents an embodiment of the method. The method is provided by way of example, as there are a variety of ways to carry out the method. The method described below can be carried out using the configurations illustrated in FIG. 2, for example, and various elements of these figures are referenced in explaining the example method. Each block shown in FIG. 4 may represent one or more processes, methods, or subroutines, carried out in the example method. Furthermore, the order of blocks is illustrative only and the order of the blocks can be changed. Additional blocks can be added or fewer blocks may be utilized, without departing from this disclosure. The behavior tracking method may begin at block S21.

In block S21, the first sensing module 11 senses posture information of an object within a tracking area to generate posture sensing signals. The wearable device 30 is worn by the object.

In one embodiment, the tracking device 20 may comprise the first sensing module 11, the second sensing module 12, the wireless communication module 13, the processing module 14, the communication module 15, the alarm module 16, and the storage module 17. The first sensing module 11 may comprise a millimeter wave sensor. The posture information can comprise a walking state, a lying state, or a standing state.

In block S22, the wireless communication module 13 acquires wireless signals of the wearable device 30 and obtains changes in position of the object according to signal strength of the wireless signals of the wearable device 30 worn by the object.

In one embodiment, the wireless communication module 13 may be a BLUETOOTH unit, a WI-FI unit, or a ZIGBEE unit. The wearable device 30 is carried or worn by the object. The wireless communication module 13 can acquire the wireless signals of the wearable device 30 and further obtain the changes in position of the object according to the signal strength of the wireless signals of the wearable device 30. The wireless communication module 13 can also obtain the changes in position of the object by determining whether the wireless signals sent by the wearable device 30 are received. For example, if the wireless communication module 13 does not receive the wireless signals sent from the wearable device 30, it indicates that the object may have left the tracking area. If the wireless communication module 13 receives the wireless signals sent from the wearable device 30, it indicates that the object is within the tracking area.

In block S23, the communication module 15 transmits the posture sensing signals and the changes in position of the object to the at least one server 10 to identify a behavior of the object.

In one embodiment, the communication module 15 can be a wired communication unit or a wireless communication unit. The sever 10 receives the posture sensing signals and the changes in position of the object and analyzes the received data by using an analytic algorithm or the like, to identify the behavior of the object. The analytic algorithm can be configured to analyze changes in posture and/or position. For example, the server 10 may determine whether the object is in a walking state, a lying down state, or a stationary or standing state based on the posture sensing signals. The server 10 may determine whether the object leaves the tracking area based on the posture sensing signals and the changes in position of the object.

In block S24, the server 10 determines whether the behavior of the object is abnormal.

In one embodiment, if the behavior of the object is normal, the method return to block S21 to continue monitoring the object within the tracking area. If the behavior of the object is abnormal, block S25 is performed.

In block S25, the server 10 outputs an alarm control signal to the tracking device 20.

In one embodiment, if the behavior of the object is abnormal, the server 10 outputs the alarm control signal to the tracking device 20.

In block S26, the alarm module 16 outputs alarm information to specific persons according to the alarm control signal.

In one embodiment, multiple first sensing modules 11 and multiple second sensing modules 12 are installed on walls or ceilings of multiple rooms of a specified building, such as an inpatient building of a hospital. The first sensing modules 11 and the second sensing modules 12 in different rooms or corridors have different position identification. If an object is determined to be fall, the fall area of the object can be determined according to the position identification of the first sensing module 11. The server 10 can output an alarm control signal to the tracking device 20 when an object is determined to be in an abnormal behavior. The alarm module 16 can output fall alarm information to warn the specific persons to pay attention to the object. The specific persons may be family members, nurses, caregivers, etc.

The embodiments shown and described above are only examples. Many details known in the field are neither shown nor described. Even though numerous characteristics and advantages of the present technology have been set forth in the foregoing description, together with details of the structure and function of the present disclosure, the disclosure is illustrative only, and changes may be made in the detail, including in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. A behavior tracking device configured to connect to at least one server and at least one wearable device, one of the at least one wearable device worn by an object, the behavior tracking device comprising:
    a first sensor, configured to sense posture information of the object within a tracking area to generate posture sensing signals;
    a wireless communication module, configured to acquire wireless signals of the wearable device worn by the object and obtain changes in position of the object according to signal strength of the wireless signals of the wearable device worn by the object; and
    a communication module, configured to transmit the posture sensing signals and the changes in position of the object to the at least one server to identify a behavior of the object.

2. The behavior tracking device of claim 1, further comprising a second sensor, wherein the second sensor is configured to sense body temperature information of the object, and the communication module is further configured to transmit the body temperature information to the at least one server.

3. The behavior tracking device of claim 2, wherein the first sensor is further configured to sense a distance between the object and the behavior tracking device, the communication module is further configured to transmit the distance between the object and the behavior tracking device to the at least one server.

4. The behavior tracking device of claim 3, wherein the at least one server is configured to perform a temperature compensation on the body temperature information according to the distance to obtain a body temperature of the object.

5. The behavior tracking device of claim 2, wherein the first sensor is a millimeter wave sensor, the second sensor is an infrared sensor, and the wireless communication module comprises a BLUETOOTH indoor positioning unit or a WI-FI communication unit.

6. The behavior tracking device of claim 1, wherein the first sensor is further configured to sense physiological information of the object, the communication module is further configured to transmit the physiological information to the at least one server, and the at least one server is further configured to determine whether physiological features of the object are abnormal according to the physiological information and output an alarm control signal if one of the physiological features of the object is abnormal.

7. The behavior tracking device of claim 6, wherein the physiological information comprises a heart rate or a respiratory rate.

8. The behavior tracking device of claim 1, wherein the communication module is a wired communication unit or a wireless communication unit.

9. A behavior tracking method implemented in a behavior tracking device, the behavior tracking method comprising:
    sensing posture information of an object within a tracking area and generating posture sensing signals according to the posture information, wherein a wearable device is worn by the object;
    acquiring wireless signals of the wearable device and obtaining changes in position of the object according to signal strength of the wireless signals of the wearable device; and
    transmitting the posture sensing signals and the changes in position of the object to at least one server to identify a behavior of the object.

10. The behavior tracking method of claim 9, further comprising:
    sensing body temperature information of the object; and
    transmitting the body temperature information to the at least one server.

11. The behavior tracking method of claim 10, further comprising:
    sensing a distance between the object and the behavior tracking device; and
    transmitting the distance between the object and the behavior tracking device to the at least one server.

12. The behavior tracking method of claim 11, wherein the at least one server performs a temperature compensation on the body temperature information according to the distance to obtain a body temperature of the object.

13. The behavior tracking method of claim 10, wherein the step of sensing the body temperature information of the object is executed by an infrared sensor.

14. The behavior tracking method of claim 9, wherein the step of sensing the posture information of the object within the tracking area and generating the posture sensing signals according to the posture information are executed by a millimeter wave sensor.

15. The behavior tracking method of claim 9, wherein the step of acquiring the wireless signals of the wearable device and obtaining the changes in position of the object according to the signal strength of the wireless signals of the wearable device are executed by at least one BLUETOOTH indoor positioning unit or at least one WI-FI communication unit.

16. The behavior tracking method of claim 9, further comprising:
    sensing physiological information of the object; and
    transmitting the physiological information to the at least one server.

17. The behavior tracking method of claim 16, wherein the physiological information comprises a heart rate or a respiratory rate, and the at least one server determines whether physiological features of the object are abnormal according to the physiological information and outputs an alarm control signal if one of the physiological features of the object is abnormal.

18. The behavior tracking method of claim 9, wherein the step of transmitting the posture sensing signals and the changes in position of the object to the at least one server is executed by a wired communication unit or a wireless communication unit.

* * * * *